(12) United States Patent
Kim et al.

(10) Patent No.: US 12,198,815 B2
(45) Date of Patent: Jan. 14, 2025

(54) UROGENITAL REPRODUCTIVE AND SEXUAL HEALTH TESTING DEVICE

(71) Applicants: Denisa Kim, Roxbury, MA (US); Calin Marin, Roxbury, MA (US)

(72) Inventors: Denisa Kim, Roxbury, MA (US); Calin Marin, Roxbury, MA (US)

(73) Assignee: Anteros Bio, Inc., Dover, DE (US)

( * ) Notice: Subject to any disclaimer, the term of this patent is extended or adjusted under 35 U.S.C. 154(b) by 0 days.

(21) Appl. No.: 18/088,655

(22) Filed: Dec. 26, 2022

(65) Prior Publication Data

US 2024/0212853 A1 Jun. 27, 2024

(51) Int. Cl.
*G16H 50/30* (2018.01)
*G16H 50/20* (2018.01)
*A61B 5/00* (2006.01)

(52) U.S. Cl.
CPC ............ *G16H 50/30* (2018.01); *G16H 50/20* (2018.01); *A61B 5/0022* (2013.01)

(58) Field of Classification Search
None
See application file for complete search history.

(56) References Cited

U.S. PATENT DOCUMENTS

| | | | |
|---|---|---|---|
| 2001/0023419 A1* | 9/2001 | Lapointe | G16H 50/20 706/15 |
| 2016/0324506 A1* | 11/2016 | Tariyal | A61B 5/150755 |
| 2017/0002432 A1* | 1/2017 | Apte | A61B 10/0096 |
| 2017/0370930 A1* | 12/2017 | Bearinger | G01N 33/53 |
| 2019/0125316 A1* | 5/2019 | Tariyal | A61B 10/0045 |
| 2022/0170915 A1* | 6/2022 | Van Den Boom | G16H 10/40 |
| 2022/0273269 A1* | 9/2022 | Capodilupo | A61B 5/6801 |

* cited by examiner

*Primary Examiner* — Benjamin S Melhus
(74) *Attorney, Agent, or Firm* — Edmond DeFrank

(57) ABSTRACT

The embodiments disclose a method including receiving, with a first memory device, user profile data including demographics from at least from two persons, receiving specimen samples of personal tissue and pelvic fluid from the at least two persons, analyzing, with a first processor, the specimen samples to identify test results including hormones, infectious diseases, PH levels and genetic disorders, comparing, with a second processor, the test results to determine any correlation information with predetermined medical conditions data, converting, with a third processor, the correlation information into recommendation data for each person, and transmitting, with a platform communication device, the recommendation data to each person via a respective wellness app operating on a mobile device of each person.

13 Claims, 10 Drawing Sheets

UROGENITAL REPRODUCTIVE AND SEXUAL HEALTH TESTING DEVICE

BACKGROUND

Romantic relationships between couples can become difficult when health issues arise with one or both of the partners. One partner may be diagnosed with a serious condition but doesn't want to burden their partner with the news. Couples having difficulty in having children may wonder which partner is perhaps unable to produce a child. One partner may have doubts about the other partner's past and potential transmittable health issues that may be passed on. What is needed is a process in which as a couple they can get answers that while private can be done jointly to ascertain if any of their concerns are valid and if so, what can be done to overcome the issue or get medical treatment for the condition. Not knowing and persistent worry, in some cases, can negatively affect the romance in the relationship.

DETAILED DESCRIPTION OF THE INVENTION

In a following description, reference is made to the accompanying drawings, which form a part hereof, and in which is shown by way of illustration a specific example in which the invention may be practiced. It is to be understood that other embodiments may be utilized, and structural changes may be made without departing from the scope of the present invention.

General Overview

It should be noted that the descriptions that follow, for example, in terms of sexual wellness kits method and devices is described for illustrative purposes and the underlying system can apply to any number and multiple types of couple partners. In one embodiment of the present invention, the sexual wellness kits method and devices can be configured using a swab. The sexual wellness kits method and devices can be configured to include pH strips and can be configured to include urine cups using the present invention.

Figure 1:
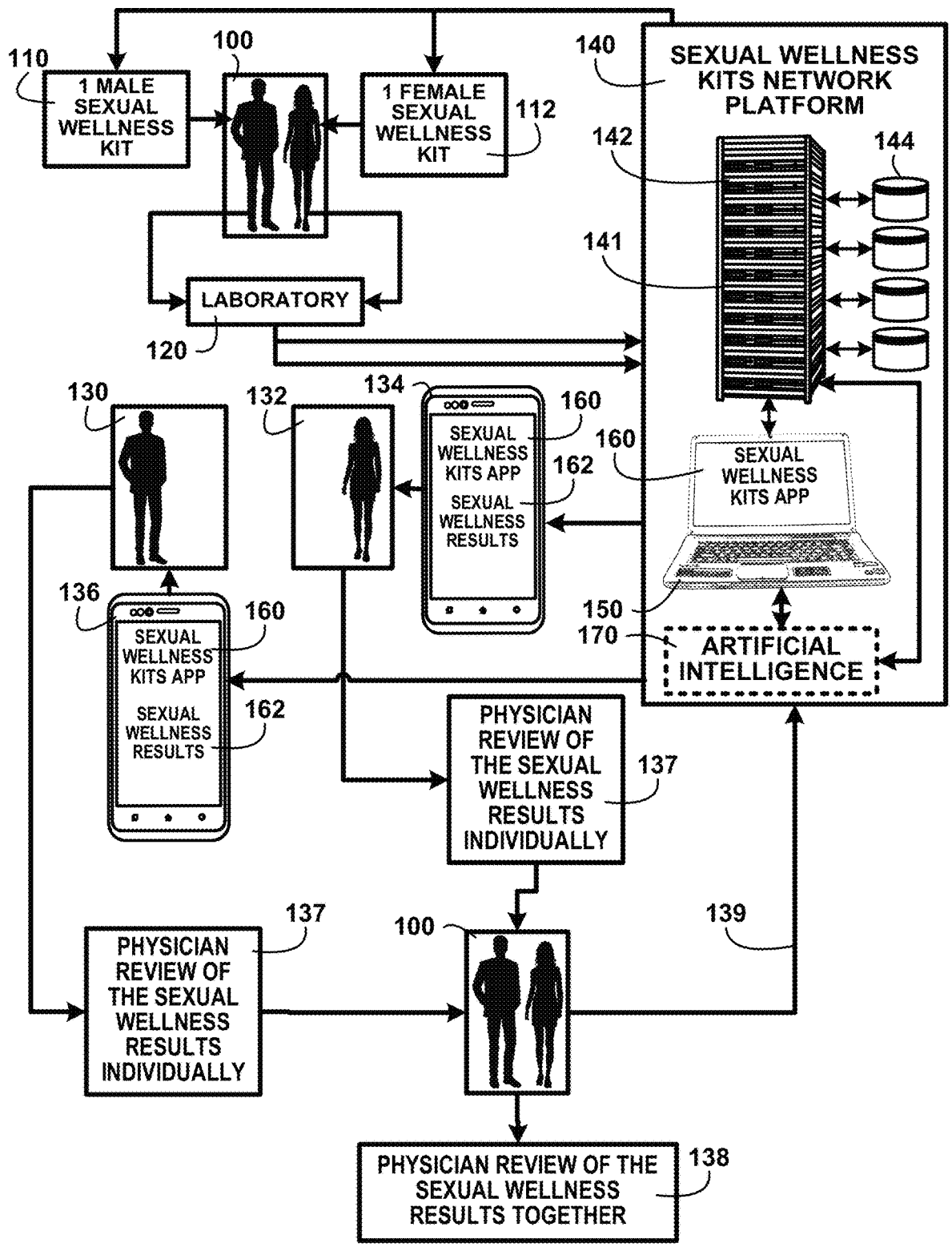
FIG. 1 shows for illustrative purposes only an example of an overview of sexual wellness kits of one embodiment.

FIG. 1 shows for illustrative purposes only an example of an overview of an electronic platform for sexual wellness kits that are computer and mobile application connected in one embodiment. FIG. 1 shows a heterosexual couple 100 receiving one male sexual wellness kit 110 and one female sexual wellness kit 112. The wellness kits 110 and 112 are computer and mobile application connected. The smart sexual wellness kits can be ordered through a sexual wellness kits network platform 140 website. The sexual wellness kits network platform 140 includes at least one server 142, a plurality of processors 141, a plurality of databases 144, a network computer 150, a sexual wellness kits app 160, and artificial intelligence 170.

In this embodiment, the heterosexual couple 100 enters their identification information including name, gender, age, demographics, ethnicity, nationality and other information that may relate to genetic factors that can determine medical conditions. Certain ethnic populations have a higher rate of specific medical conditions that may be reflected in the laboratory 120 tests. The heterosexual couple 100 personal data will be stored on the sexual wellness kits network platform 140 plurality of databases 144. The sexual wellness kits app 160 can be downloaded from the network computer 150 to a female partner smart phone 134 and a male partner smart phone 136.

When the samples have been taken and mailed to a laboratory 120, the laboratory performs various tests for infections and other risks and fertility tests. Both the male partner 130 and female partner 132 submit samples for testing. The laboratory 120 files on the sexual wellness kits network platform 140 at least one server 142 the testing results identified for each partner of the couple. The sexual wellness kits network platform 140 plurality of processors 141 and artificial intelligence 170 compares the laboratory 120 test results with the stored partner personal data stored on the sexual wellness kits network platform 140 plurality of databases 144. The artificial intelligence 170 using stored genetic ethnicity conditions from the plurality of databases 144 makes a comparison of the partner personal data and the laboratory 120 test results to determine whether any detected conditions correlate to any known genetic ethnicity conditions.

Additionally, the artificial intelligence 170 converts the raw third party laboratory 120 test results data into layman terms with explanations that make it more easily interpreted and understood by the partners in the couple. Converting the raw third party laboratory test results data into layman terms includes the typical lab results set of numbers known as a reference range. A reference range is referred to as "normal values." For example the results may show test results: "normal: 77-99 mg/dL" (milligrams per deciliter). Reference ranges are based on the normal test results of a large group of healthy people. The range shows approximate highs and lows of a normal result. Healthy people get results outside the reference range, while people with health problems can have results in the normal range.

If the lab results fall outside the reference range, or if symptoms are presented despite a normal result, additional testing may be recommended. Reference ranges may also include terms for example negative or normal, which means a disease or substance being tested was not found and the terms positive or abnormal, which means the disease or substance was found. A result may note, the result was inconclusive or uncertain, which means there wasn't enough information in the results to diagnose or rule out a disease. An inconclusive result may indicate additional testing may be recommended.

Tests that measure various organs and systems often give results as reference ranges, while tests that diagnose or rule out diseases often use the terms listed above. The plurality of databases 144 stores processor updates of diseases and substances including for example hormones and symptoms and for examples vital signs measurements associated with the stored diseases and substances. The layman's terms provide explanations of what the results may indicate and potential diseases and substances the test results indicate may be present.

The possible symptoms, the person's vital signs and test results may indicate the presence of a disease or substances transmitted to the person may include a recommendation to visit a physician to investigate further. The converted test results are not provided to be a diagnosis or medical opinion but rather the possible meaning of the testing and personal data obtained from sensors and the persons self-testing for example a pH level test and self-reported conditions at the time the test samples were taken. The plurality of sensors detects and measures a partner's vital signs and other physiological factors related to their wellness levels.

The explanations further point out that test results can be skewed by certain foods and drinks, medicines, stress, vigorous exercise, variations in lab procedures and having an illness. The sexual wellness results 162 converted into layman's term is transmitted to each partner for their individual sexual wellness results 162 via the sexual wellness kits app 160.

Further, the artificial intelligence 170 and network computer 150 matches the raw laboratory 120 test results data with generally accepted suggestions for possible over the counter supplements with research backed ingredients to help remediate common symptoms, a list of prevalent similar conditions considered top disruptors, and for serious risk detected conditions and provide an advisory to visit a physician to review the results. The sexual wellness results 162 are transmitted via the sexual wellness kits app 160.

A physician may review the sexual wellness results individually 137 with each partner separately. If the partners are willing to have a physician review sexual wellness results together 138, the physician can provide explanations of each partner's conditions and possible treatments to relieve the conditions. The physician can store the reviews 139 in the plurality of databases 144. This mutual understanding can dispel many of the concerns and provide guidance on how the partners can assist each other in improving the health of each other. The physician can discuss the laboratory 120 genetic testing which may be part of the basis for a condition to be present.

Additionally, the test may reveal reasons for difficulties in getting a pregnancy. In many cases, wellness may be improved with changes in diet and nutritional deficiency improvements with vitamin and mineral supplements indicated by the results. The sexual wellness kits can also provide benefits in the couple's relationship by means of bringing enlightenment to issues that have been lurking in the shadows and causing concerns of one embodiment.

DETAILED DESCRIPTION

Figure 2:
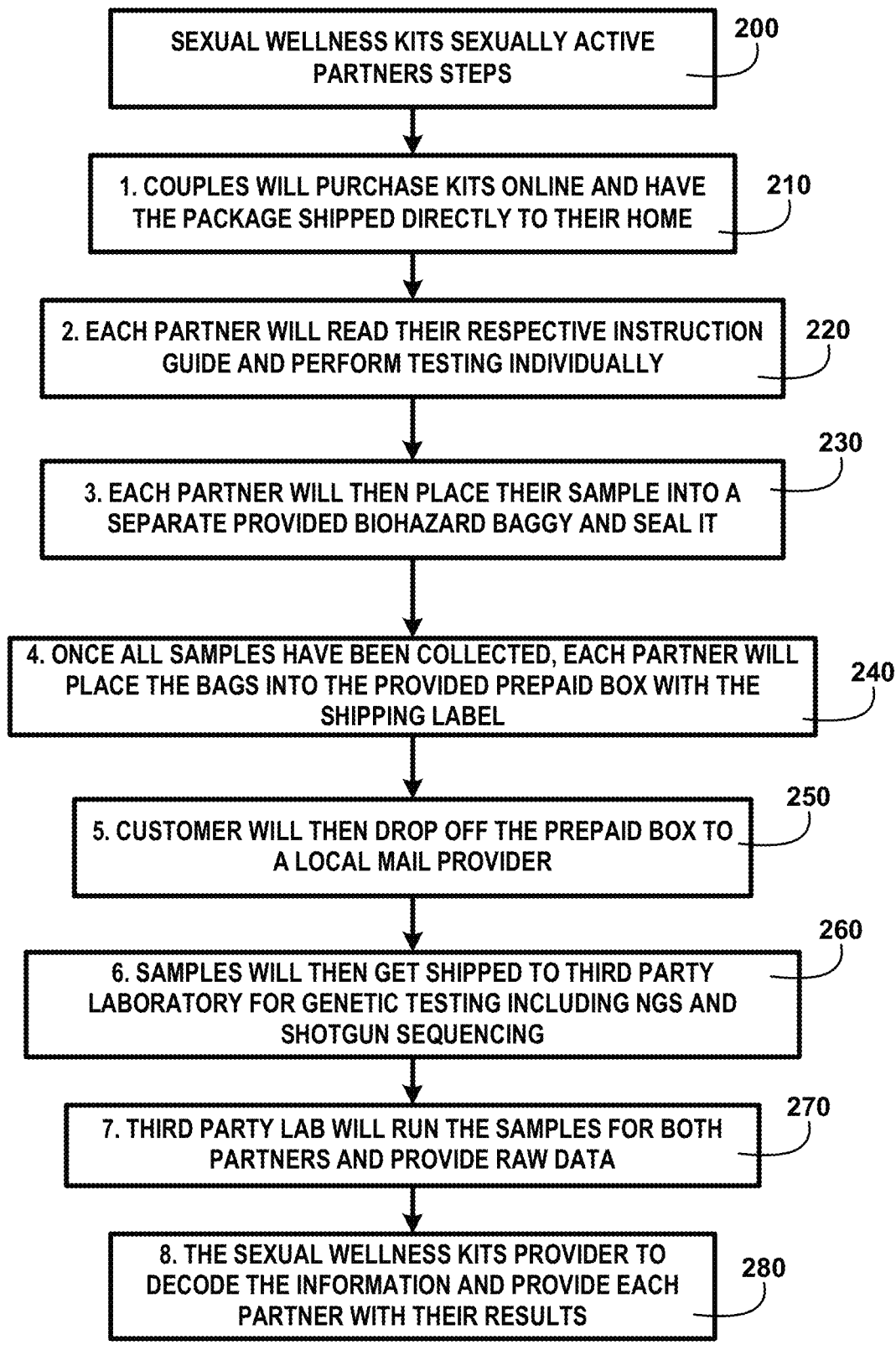
FIG. 2 shows for illustrative purposes only an example of sexual wellness kits sexually active partners of one embodiment.

FIG. 2 shows for illustrative purposes only an example of sexual wellness kits sexually active partners of one embodiment. FIG. 2 shows sexual wellness kits sexually active partner steps 200 the partners will follow to effectively utilize the sexual wellness kits. The steps provide guidance on the proper collection of the samples and handling of the sample packaging to provide uncontaminated samples for the laboratory 120 of FIG. 1 testing.

The steps include the following sequence: Step 1. Couples will purchase kits online and have the package shipped directly to their home 210. Step 2. Each partner will read their respective instruction guide and perform testing individually 220. Step 3. Each partner will then place their sample into a separate provided biohazard baggy and seal it 230. Step 4. Once all samples have been collected, each partner will place the bags into the provided prepaid box with the shipping label 240. Step 5. Customer will then drop off the prepaid box to a local mail provider 250. Step 6. Samples will then get shipped to third party laboratory for genetic testing including Next-Generation Sequencing (NGS) and shotgun sequencing 260. Step 7. A third party lab will run the samples for both partners and provide raw data 270. Step 8. The sexual wellness kits provider decodes the raw data information and provides each partner with their results 280 via the sexual wellness kits network platform website and/or the downloadable sexual wellness kits app. The sexual wellness kits provider decoding of the laboratory 120 of FIG. 1 provides results information in layman's terms with brief explanations of the goals of the test and meaning of the results compared to what is accepted as clinically normal ranges of results for that particular test.

In Step 6, samples will then get shipped to third party laboratory for genetic testing including NGS and shotgun sequencing 260 most people would not have knowledge of NGS or shotgun sequencing. In this specific example an explanation of the testing and its purpose are provided to assist the partners in understanding what the testing consists of and its purpose. Each person is made up of cells in our skin, hair, organs and our entire body. The cells include a molecule inside cells that contain the genetic information responsible for the development and function of each individual. The molecules are called DNA molecules for Deoxyribonucleic Acid (abbreviated DNA).

The DNA molecules allow this information to be passed from one generation to the next. A portion of the DNA molecules from the mother and father is passed from the adults to their offspring (children) during reproduction. DNA is made of two linked strands that wind around each other to resemble a twisted ladder, a shape known as a double helix. Sequencing is a process that tracks the precise order of nucleotides in a gene, a cluster of genes, chromosome, and a complete genome or set of chromosomes. They are the carriers of fundamental genetic information and create the distinctive characteristics or qualities of someone.

It has been found that certain populations have a prevalence of a genetic disorder, a condition or a disease caused in whole or in part by a change in the DNA sequence away from the normal sequence. These genetic disorders, conditions or diseases began hundreds and thousands of years earlier. The DNA genetic disorder was passed on due to geographic isolation of the population in ancient times.

DNA is made up of four building blocks called nucleotides: adenine (A), thymine (T), guanine (G), and cytosine (C). The nucleotides attach to each other (A with T, and G with C) to form chemical bonds called base pairs, which connect the two DNA strands. It is very important in genomic studies, forensic studies, virology, biological systematic, medical diagnosis, biotechnology and in many other fields to analyze the structure and function of genes and identification of organisms. Furthermore, there are different types of sequencing methods available. Shotgun Sequencing and Next Generation Sequencing (NGS) are two advanced methods among them.

Shotgun sequencing is a sequencing method which randomly breaks up DNA sequences into many small fragments and reassembles the sequence by observing the overlapping regions. Next Generation Sequencing (NGS) is an advanced method of genetic sequencing which depends on capillary electrophoresis. Capillary electrophoresis is an analytical technique with the use of an applied voltage.

The sexual wellness kits laboratory testing 120 of FIG. 1 can identify genetic characteristics of each partner that may include a genetic disorder that would be responsible for a partner's medical condition. The sexual wellness kits network platform 140 of FIG. 1 has a plurality of databases 144 of FIG. 1 that includes a library of genetic disorders. The sexual wellness kits network platform 140 of FIG. 1 includes artificial intelligence 170 of FIG. 1 that analyzes the genetic sequencing test results to determine any matches to known genetic disorders in the library. Fortunately, many treatments have been developed to relieve the symptoms and conditions caused by the genetic disorders.

In another example, testing of the sexual wellness kits laboratory 120 of FIG. 1 can identify vitamin and mineral deficiencies that can cause conditions including infertility. For example, studies have shown that a Vitamin D deficiency is one reason for fertility problems and undesirable pregnancy outcomes. Vitamin D deficiency is also associated with low Vitamin D levels in breast milk. Several studies have shown that Vitamin D has the potential to improve both semen quality and ovarian stimulation. Vitamin D appears to be linked to both better fertility and a healthier pregnancy for women. Some studies have suggested that healthy levels of Vitamin D can improve the success of In Vitro Fertilization (IVF) and the transfer of frozen donor egg embryos. Vitamin D sufficient levels in the blood have been associated with higher pregnancy rates in women, as opposed to those with lower levels. Studies have shown that women with normal levels of Vitamin D are four times more likely to conceive through IVF than those with low levels.

Investigations have shown that pregnant women with higher levels of Vitamin D had greater live birth rates than those with lower levels. High levels of Vitamin D may not increase fertility; the evidence seems to suggest that deficiencies can be detrimental to fertility and healthy pregnancies. The sexual wellness kits test results in layman's terms provide information as described above to inform the partner(s) an understandable explanation of the testing results.

In addition, the generally accepted suggestions transmitted with the sexual wellness kits app 160 of FIG. 1 include the artificial intelligence 170 of FIG. 1 and network computer 150 matches of the raw laboratory 120 of FIG. 1 test results data with generally accepted suggestions. For example, possible over the counter supplements with research backed ingredients to help remediate common symptoms, for example, Vitamin D3 and Vitamin D2 Supplements.

When purchasing vitamin D supplements, there may be two different forms: vitamin D2 and vitamin D3. Vitamin D2 is made from plants and is found in fortified foods and some supplements. Vitamin D3 is naturally produced in the human body and is found in animal foods. There are discussions on whether vitamin D3 "cholecalciferol" is better than vitamin D2 "ergocalciferol" at increasing blood levels of the vitamin. A meta-analysis of randomized controlled trials compared the effects of vitamin D2 and D3 supplements on blood levels found that D3 supplements tended to raise blood concentrations of the vitamin more and sustained those levels longer than D2. Some experts cite vitamin D3 as the preferred form as it is naturally produced in the body and found in most foods that naturally contain the vitamin.

Vitamin D3 can be formed when a chemical reaction occurs in human skin, when a steroid called 7-dehydrocholesterol is broken down by the sun's type B ultraviolet (UVB) light or so-called "tanning" rays, but not tanning bed generated light. The amount of the vitamin absorbed can vary widely. The following are conditions that decrease exposure to UVB light and therefore lessen vitamin D absorption: Use of sunscreen can reduce vitamin D absorption by more than 90%; Wearing full clothing that covers the skin; Spending limited time outdoors; Darker skin tones due to having higher amounts of the pigment melanin, which acts as a type of natural sunscreen; Older ages when there is a decrease in 7-dehydrocholesterol levels and changes in skin, and a population that is likely to spend more time indoors; Certain seasons and living in northern latitudes above the equator where UVB light is weaker. The body stores vitamin D from summer sun exposure, but it must last for many months. By late winter, many people are deficient. Cautionary note ultraviolet rays can cause skin cancer, avoid excessive sun exposure and in general, tanning beds should not be used.

Vitamin D deficiency may occur from a lack in the diet, poor absorption, or a metabolic need for higher amounts. If one is not eating foods with enough vitamin D, a deficiency may arise. People who cannot tolerate or do not eat milk, eggs, and fish, such as those with a lactose intolerance or who follow a vegan diet, are at higher risk for a vitamin D deficiency. Other people at high risk of vitamin D deficiency include:

A vitamin D deficiency occurs in people with inflammatory bowel disease (ulcerative colitis, Crohn's disease) or other conditions that disrupt the normal digestion of fat. Vitamin D is a fat-soluble vitamin that depends on the gut's ability to absorb dietary fat. People who are obese tend to have lower blood vitamin D levels. Vitamin D accumulates in excess fat tissues but is not easily available for use by the body when needed. Higher doses of vitamin D supplementation may be needed to achieve a desirable blood level. Conversely, blood levels of vitamin D rise when obese people lose weight. A vitamin D deficiency occurs in people who have undergone gastric bypass surgery, which typically removes the upper part of the small intestine where vitamin D is absorbed.

The raw laboratory 120 of FIG. 1 test results may reveal conditions resulting from prolonged vitamin D deficiency including: Rickets: A condition in infants and children of soft bones and skeletal deformities caused by failure of bone tissue to harden. Osteomalacia: A condition in adults of weak and softened bones that can be reversed with supplementation. This is different than osteoporosis, in which the bones are porous and brittle and the condition is irreversible. A cautionary note regarding Vitamin D Toxicity is included in the sexual wellness kits suggestions. Vitamin D toxicity most often occurs from taking supplements. The low amounts of the vitamin found in food are unlikely to reach a toxic level, and a high amount of sun exposure does not lead to toxicity because excess heat on the skin prevents D3 from forming. It is advised to not take daily vitamin D supplements containing more than 4,000 IU unless monitored under the supervision of your doctor.

The sexual wellness kits also describe symptoms of vitamin D toxicity. Those symptoms of vitamin D toxicity include anorexia, weight loss, and an irregular heartbeat or pulse, and hardening of blood vessels and tissues due to increased blood levels of calcium, potentially leading to damage of the heart and kidneys. Exposure to the sun's rays in a sunny office or driving in a car won't help to obtain vitamin D as window glass completely blocks UVB ultraviolet light.

An addition to or change in a person's diet can assist in relief of a vitamin D deficiency. Some foods that are high in Vitamin D include cod liver oil, salmon, swordfish, tuna fish, orange juice fortified with vitamin D, Dairy and plant milks fortified with vitamin D, sardines, beef liver, egg yolk, and fortified cereals. The detection of a vitamin D deficiency and other similar conditions may provide motivation to the partner to investigate research on vitamin D and specific health conditions and diseases including Bone health and muscle strength, Cancer, Heart disease, Type 2 diabetes, Immune function, Risk of premature death, and Cognitive decline if indicated by the sexual wellness kits laboratory 120 of FIG. 1 test results.

The sexual wellness kits laboratory 120 of FIG. 1 test results includes a list of prevalent similar conditions considered top disruptors. A listing of top disrupters will demonstrate to the partner that others have experienced similar difficulties and been successful in overcoming and dealing with the conditions. This provides some relief that the partner is not alone in facing the conditions and medical attention and progress has been found or under investigation of the same or similar conditions, in other words help is here or on the way.

The sexual wellness kits laboratory 120 of FIG. 1 test results and layman's terms conversion provides more than knowledge of how a partner can improve their health issues. The knowledge provided of the conditions, possible causes and remedies also contributes to the mental and emotional health of the partner. The couple will get an improved understanding of the issues and possible solutions which can lead to a more open relationship where the partners can help one another deal with the issues and regain the closeness that may have faltered due to a lack of discussion of the conditions and their effects on the couple's emotional condition of one embodiment.

Figure 3:
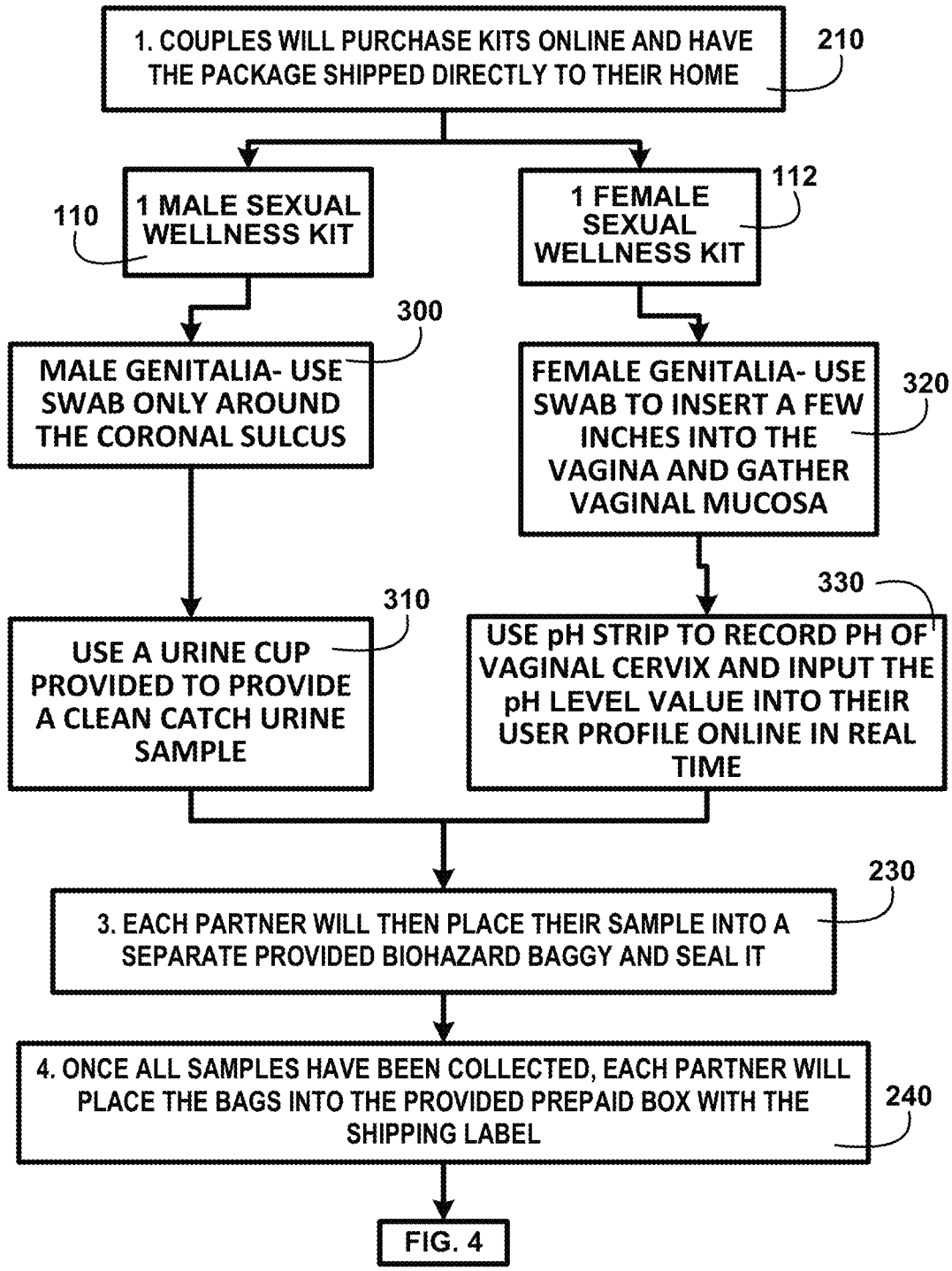
FIG. 3 shows for illustrative purposes only an example of sexual wellness kits sexually active partners steps of one embodiment.

Sexual Wellness Kits Sexually Active Partner Steps:

FIG. 3 shows for illustrative purposes only an example of sexual wellness kits sexually active partners steps of one embodiment. FIG. 3 shows more details included in the sexual wellness kits sexually active partner steps. In Step 1. Couples will purchase kits online and have the package shipped directly to their home 210. In this example of a purchase of the sexual wellness kits by a heterosexual couple, the one male sexual wellness kit 110 includes the instruments for collecting a sample and instructions for male genitalia-use swab only around the coronal sulcus 300. An additional procedure instruction directs the male partner to use a urine cup provided to provide a clean catch urine sample 310.

Additionally, the purchase will include one female sexual wellness kit 112 that includes the instruments for collecting a sample and instructions for female genitalia-use swab to insert a few inches into the vagina and gather vaginal mucosa 320. An additional procedure instruction directs the female partner to use pH strip to record pH of vaginal cervix and input the pH level value into their user profile online in real time 330. Step 3. Each partner will then place their sample into a separate provided biohazard baggy and seal it 230. Step 4. Once all samples have been collected, each partner will place the bags into the provided prepaid box with the shipping label 240. Additional step details continue on FIG. 4.

In one example of the instructions the female sexual wellness kit 112 includes partner information on the reasons for checking pH in women with normal and abnormal vaginal microbiota. Healthy women of reproductive age have a vaginal pH level around 4.50. A shift in the vaginal microbiota may result in an elevated pH in the upper genital tract. This might contribute to decreased fertility and increased risk of premature birth of the child. Therefore, the sexual wellness kit measurement of the pH level of the vagina can ascertain whether the female partner has a normal or abnormal vaginal microbiota.

A normal vaginal microbiota pH level in studies was found to be most acidic in the lower vagina. Women with an abnormal vaginal microbiota had an increased pH in the lower vagina compared to the other groups. Although not conclusive of an abnormal condition as the vagina has a variable pH level range, it may need further review by a physician to determine if any abnormality is detected. The variable pH level range of the vagina is not disrupted in women with an abnormal vaginal microbiota.

However, disturbance in the normal vaginal flora affects the health of a woman and, in pregnancy, her fetus and newborn child. A disturbance in the normal vaginal flora is the predominant cause of genital complaints in women of childbearing age worldwide. A condition of disturbance in the normal vaginal flora can indicate possible bacterial vaginosis (BV). BV is associated with pelvic inflammatory disease, infertility, spontaneous abortion, and preterm birth. If the female partner is pregnant the stability of the microbiota becomes more stable during pregnancy. Should the pH level be elevated the female sexual wellness kit 112 results will advise the female partner to consult with her physician for further review and testing of one embodiment.

Figure 4:
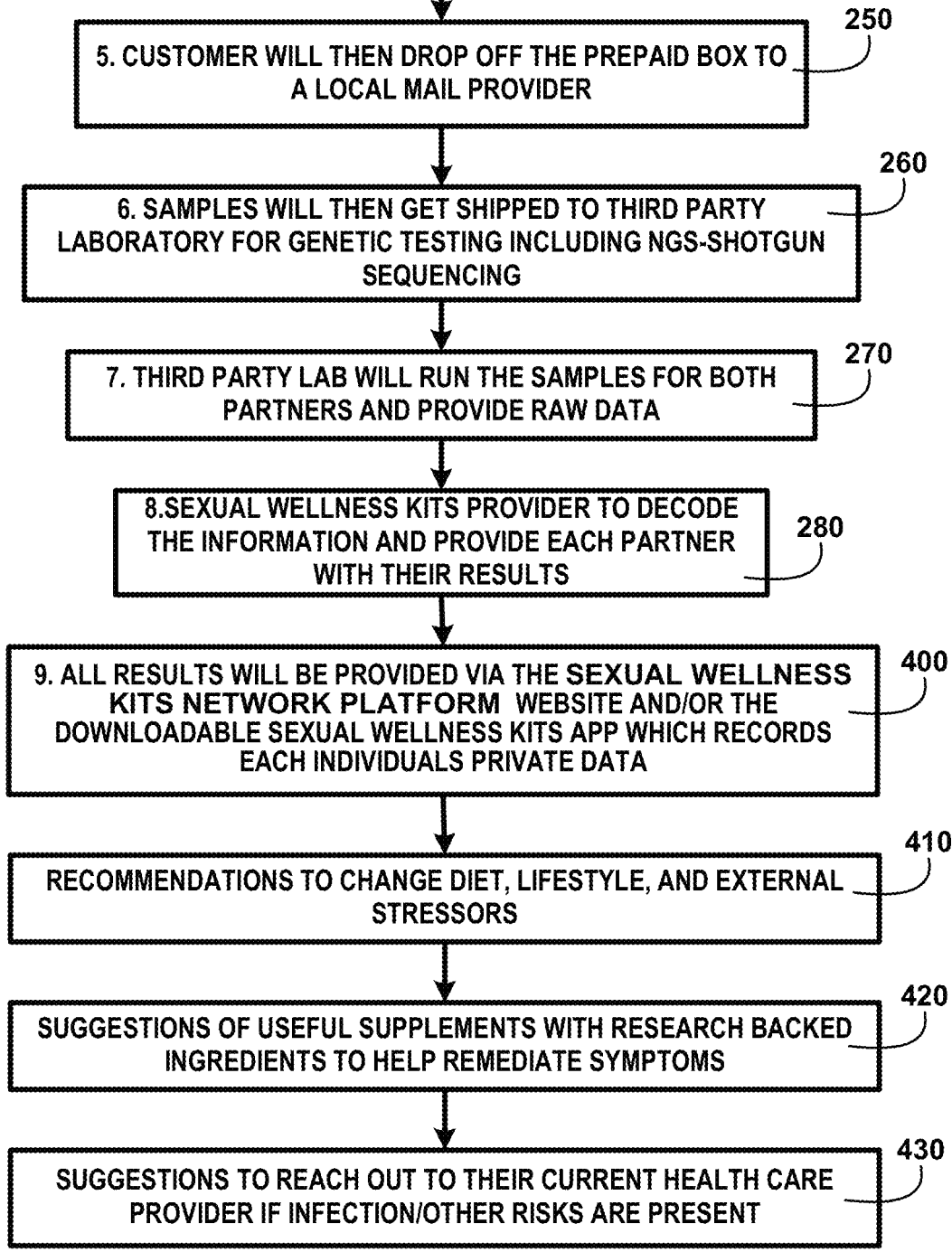
FIG. 4 shows for illustrative purposes only an example of sexual wellness kits sexually active partner steps continued of one embodiment.

Sexual Wellness Kits Sexually Active Partners Steps Continued:

FIG. 4 shows for illustrative purposes only an example of sexual wellness kits sexually active partner steps continued of one embodiment. FIG. 4 shows a continuation from FIG. 3 with Step 5. Customer will then drop off the prepaid box to a local mail provider 250. Step 6. Samples will then get shipped to third party laboratory for genetic testing including NGS-shotgun sequencing 260. Step 7. Third party lab will run the samples for both partners and provide raw data 270. Step 8. Sexual wellness kits provider to decode the information and provide each partner with their results 280. Step 9. All results will be provided via the sexual wellness kits network platform website and/or the downloadable sexual wellness kits app which records each individual's private data 400. The results may include recommendations to change diet, lifestyle, and external stressors 410 to reduce or reverse condition symptoms.

The results may include suggestions of useful supplements with research backed ingredients to help remediate symptoms 420. The results may include suggestions to reach out to their current health care provider if infection/other risks are present 430. The results may include that the laboratory 120 of FIG. 1 results do not indicate any abnormalities, adverse conditions or any severe risk conditions. These final results should relieve the couple of any previously harbored concerns or perceived conditions affecting the health and wellness of one another of one embodiment.

Figure 5:
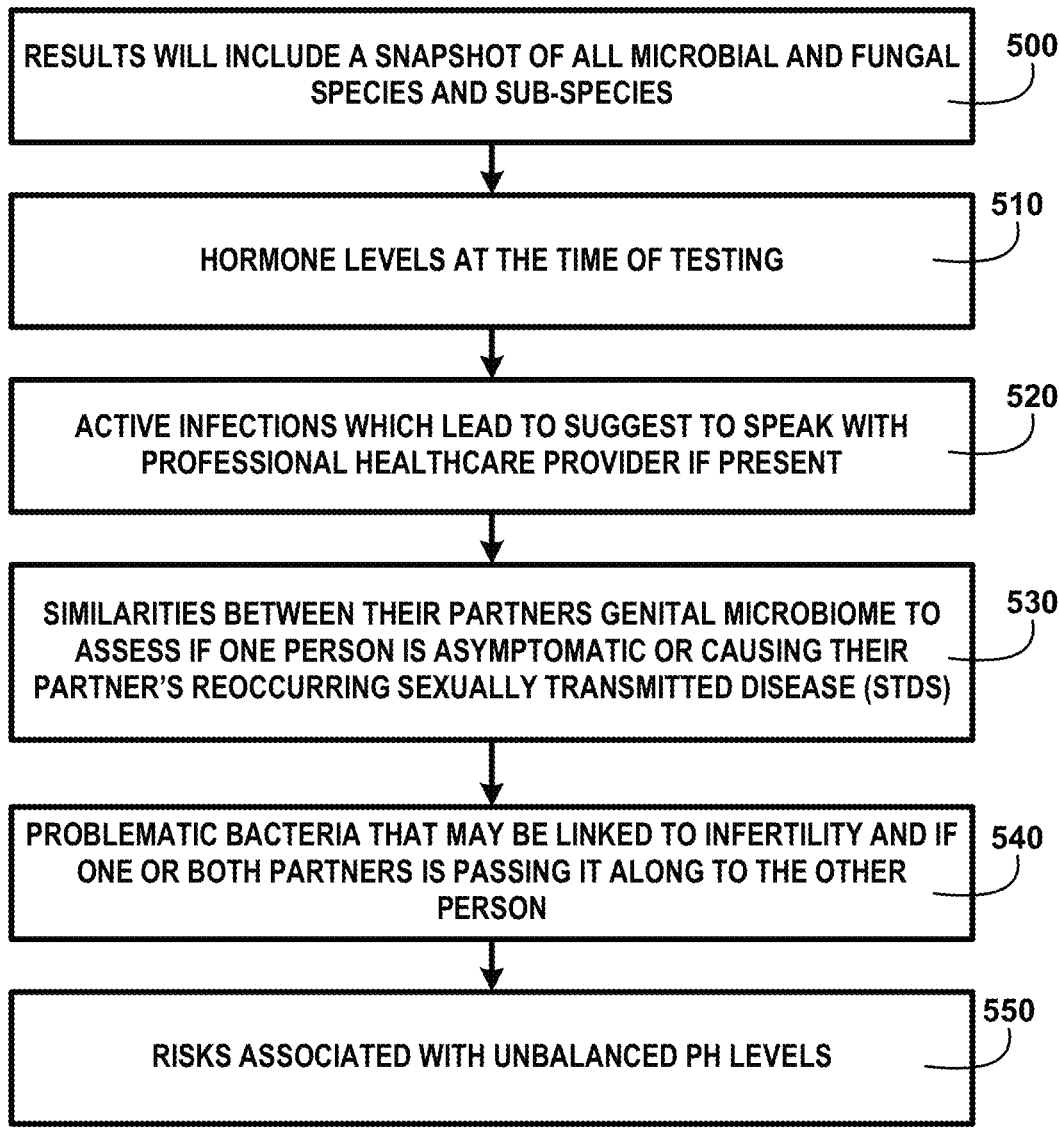
FIG. 5 shows for illustrative purposes only an example of microbial and fungal species and sub-species of one embodiment.

Microbial and Fungal Species and Sub-Species:

FIG. 5 shows for illustrative purposes only an example of microbial and fungal species and sub-species of one embodiment. FIG. 5 shows the sexual wellness kits results will include a snapshot of all microbial and fungal species and sub-species 500 detected in the laboratory 120 of FIG. 1 tests. The female sexual wellness kits female genitalia sample uses a swab to insert a few inches into the vagina and gather vaginal mucosa 320 of FIG. 3 that provides a sample used in a number of tests. The female sexual wellness vaginal swab testing includes hormone levels at the time of testing 510. The testing may detect active infections which leads to suggestions to speak with a professional healthcare provider if present 520. The testing also detects similarities between their partners genital microbiome to assess if one person is asymptomatic or causing their partner's reoccurring sexually transmitted disease (STDs) 530. Testing may detect problematic bacteria that may be linked to infertility and if one or both partners is passing it along to the other person 540. Risks associated with unbalanced PH levels 550 can also be detected with the laboratory 120 of FIG. 1 testing.

The female sexual wellness kits include information specifically related to testing results particularly analyzing female wellness issues. Some testing is applicable to both genders for example hormone level testing directed to males including testosterone and females including estrogen. In one embodiment, the sexual wellness kits include information specifically related to testing results for infertility that is a common clinical problem that affects an estimated 15% of couples worldwide. According to the 2006 National Survey of Family Growth, approximately 7.4 million women age 15-44 in the U.S. reported receiving any type of infertility service. But with current technology, women who undergo infertility treatments enjoy much improved success rates.

Infertility treatments can include a clinical evaluation, including multiple laboratory and imaging studies. Laboratory testing for female hormones is a large part in both the work up for infertility and monitoring during treatment and during in vitro fertilization (IVF) cycles. Sexual wellness kits laboratory tests used for fertility testing include Follicle Stimulating Hormone (FSH), Estradiol (E2), Anti-Müllerian Hormone, Inhibin B, Serum levels, Progesterone, Follicular phase, Secretory phase with a sample being taken one week prior to expected menses to assess for ovulation, and Lutenizing Hormone (LH).

The Sexual wellness kits laboratory tests for active infections include detection of micro-organisms. The most common micro-organisms are fungi, bacteria, archaea which are known to be beneficial rather than harmful to human health for reducing skin pH or keeping it at low levels to lower susceptibility to infections and viruses, *candida*, and viruses. For example, symptoms of infection from *Candida albicans* usually form in areas where *candida* lives naturally, including inside your mouth and throat, inside your vagina and rectum, near the diaper region on infants (genitals, buttocks, thighs), and on folds of your skin (armpits, groin, under breasts).

The symptoms of *Candida albicans* vary where in normal situations, *candida* will not cause any symptoms unless an overgrowth occurs due to an imbalance of bacteria. Symptoms of infection include skin redness (rash), itching, blisters, lumpy white patches, pain, soreness or discomfort, burning sensation, and vaginal discharge. Infections by *Candida albicans* can be caused by feeling stressed, having uncontrolled diabetes, having a weak immune system, eating a diet with excess refined carbohydrates, yeast and sugar, and taking antibiotics, steroids, hormones or oral contraceptives. *Candida albicans* is not a sexually transmitted disease or infection of one embodiment.

Figure 6:
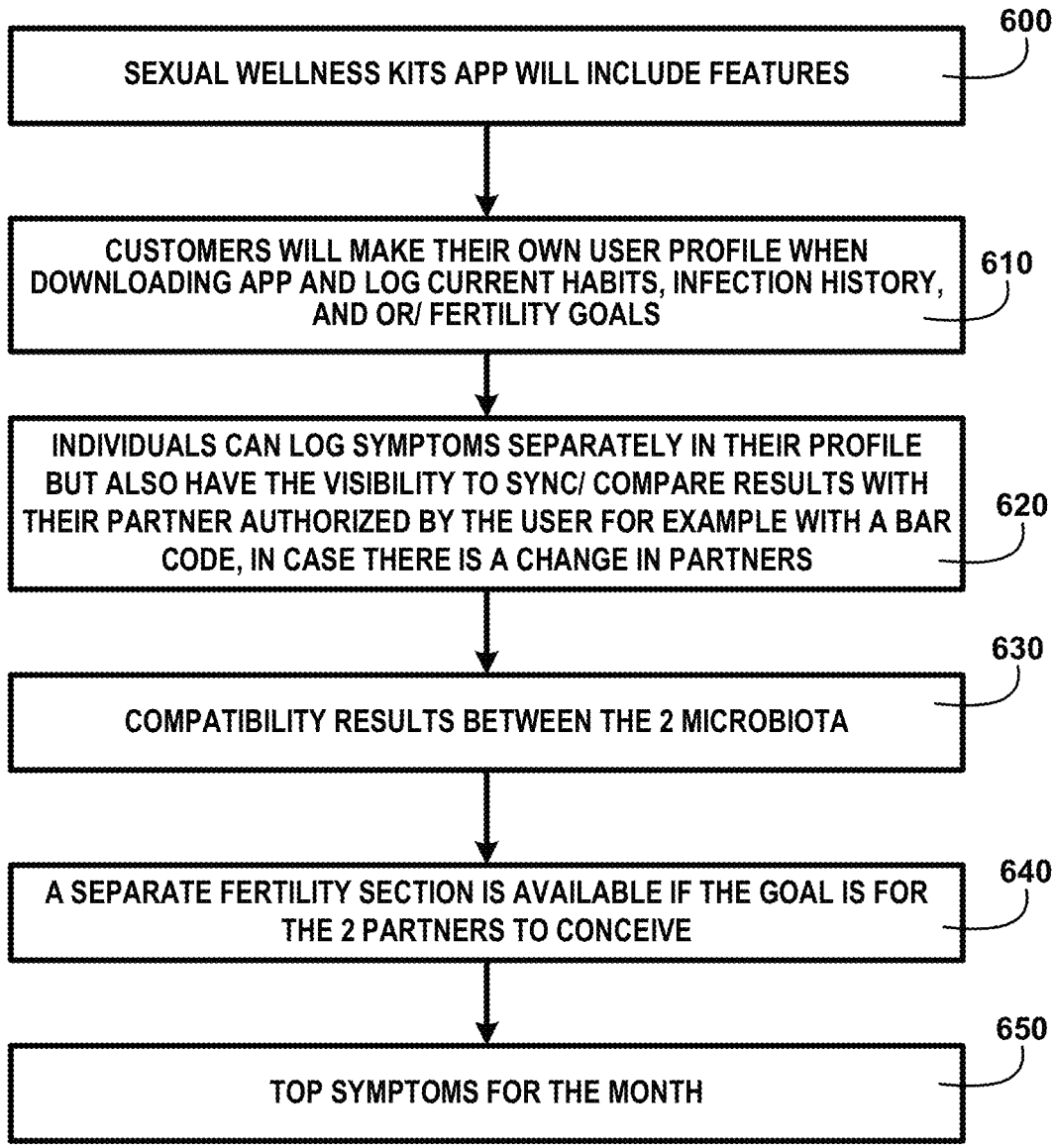
FIG. 6 shows for illustrative purposes only an example of sexual wellness kits app of one embodiment.

Sexual Wellness Kits App:

FIG. 6 shows for illustrative purposes only an example of sexual wellness kits app of one embodiment. FIG. 6 shows the sexual wellness kits app will include features 600 including customers will make their own user profile when downloading app and log current habits, infection history, and/or fertility goals 610 and demographics.

Individuals can log symptoms separately in their profile but also have the visibility to sync/compare results with their partner authorized by the user for example with a bar code, in case there is a change in partners 620. Compatibility results between the two microbiota 630 may be detected with the laboratory 120 of FIG. 1 genetic testing. For example, compatibility may be a genetic disposition to a genetic disorder that could for example endanger children conceived by the couple. A separate fertility section is available if the goal is for the two partners to conceive 640 a child. A list of top symptoms for the month 650 is provided with the sexual wellness kits results. This may provide an indication to a partner that a particular symptom is not unusual and treatable of one embodiment.

Figure 7:
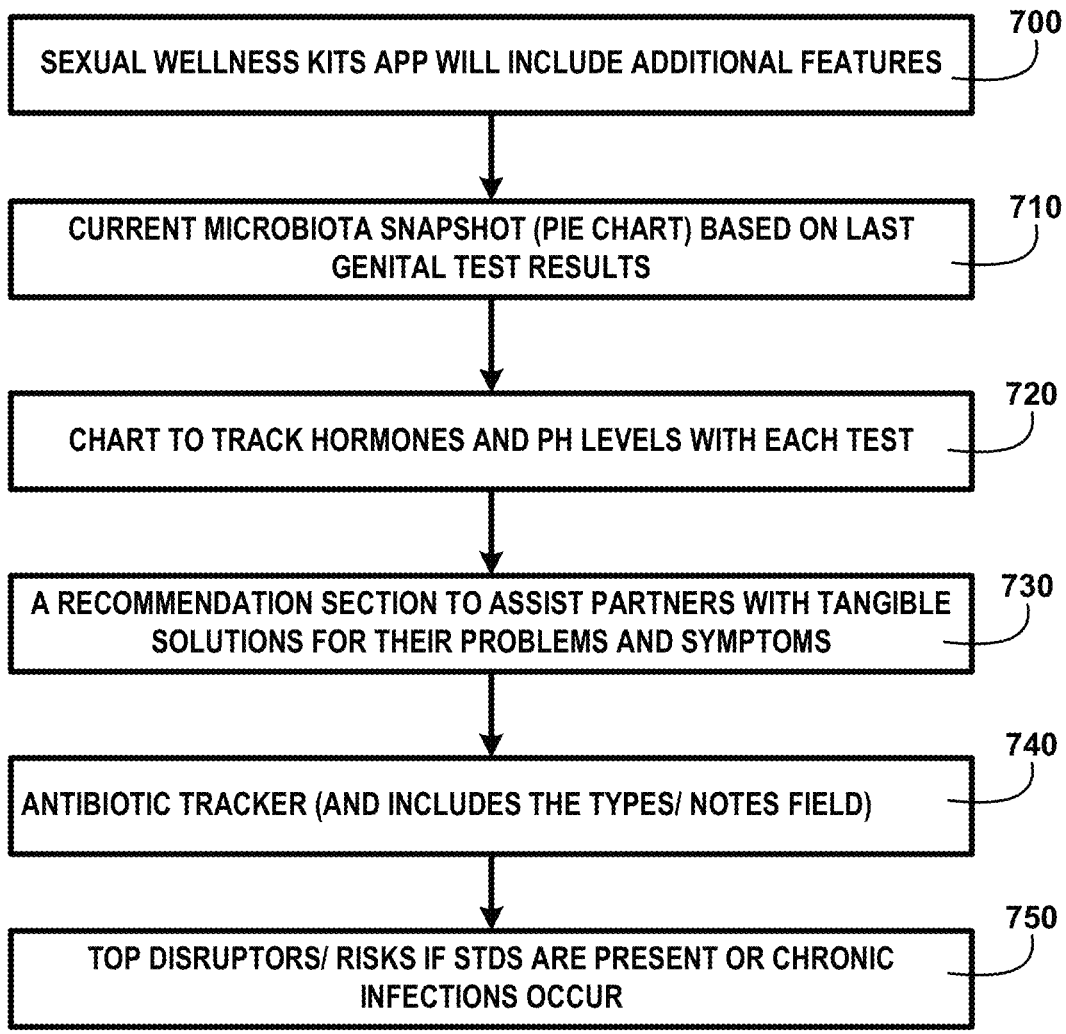
FIG. 7 shows for illustrative purposes only an example of sexual wellness kits app features of one embodiment.

Sexual Wellness Kits App Features:

FIG. 7 shows for illustrative purposes only an example of sexual wellness kits app features of one embodiment. FIG. 7 shows the sexual wellness kits app will include additional features 700 including a current microbiota snapshot (pie chart) based on last genital test results 710. The sexual wellness kits app 160 of FIG. 1 generates, with at least one of the plurality of processors 141 of FIG. 1, a chart to track hormones and pH levels with each test 720. A recommendation section to assist partners with tangible solutions for their problems and symptoms 730 accompanies the test results which can be sent to the partner via the sexual wellness kits app 160 of FIG. 1. An antibiotic tracker (and includes the types/notes field) 740 is also generated by the sexual wellness kits app 160 of FIG. 1 to assist the partner in recognizing their use of antibiotics which may affect the testing results. The sexual wellness kits app 160 of FIG. 1 also displays a listing of top disruptors/risks if STDs are present or chronic infections occur 750 to keep the partner informed of testing results of one embodiment.

Figure 8:
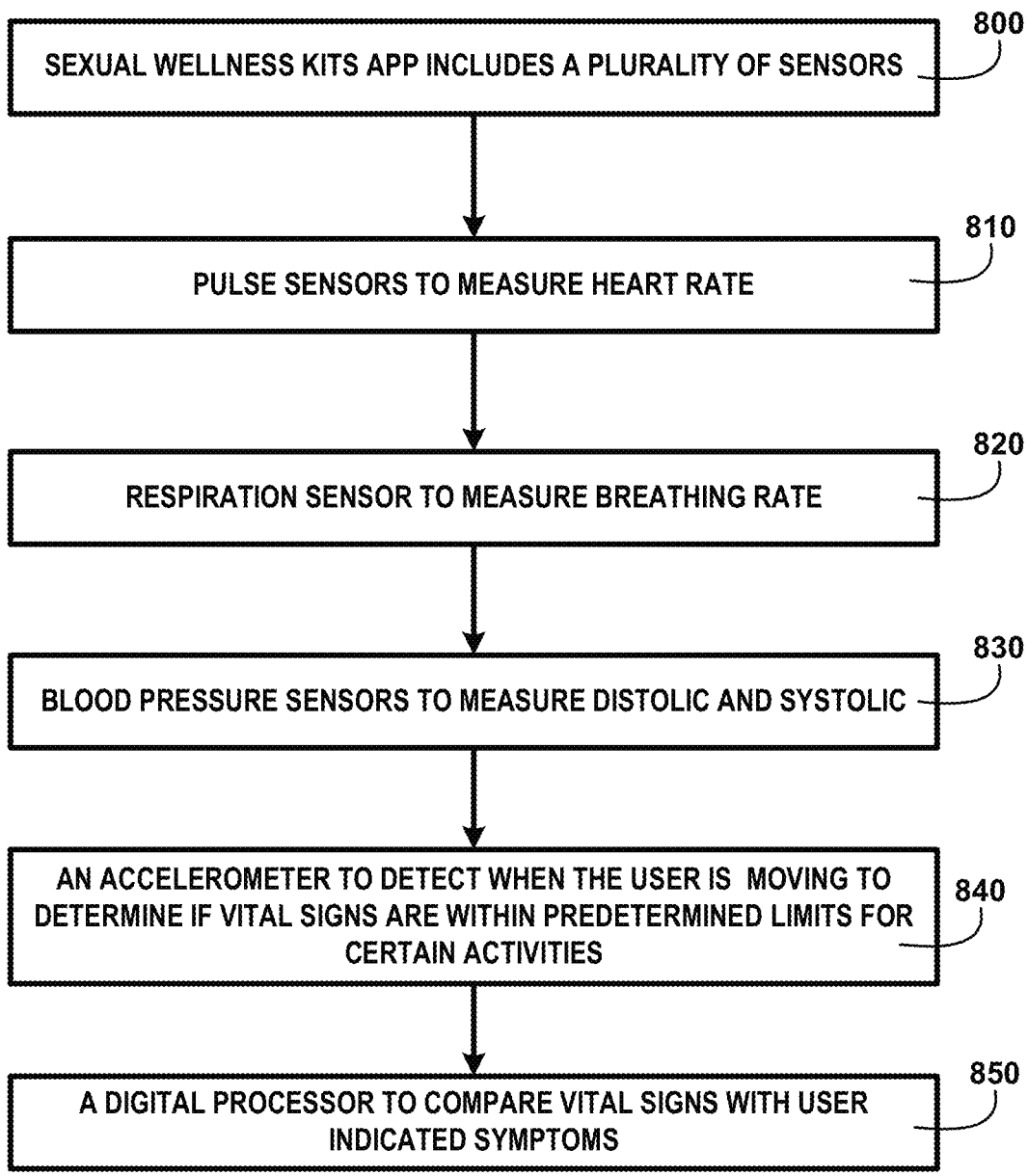
FIG. 8 shows for illustrative purposes only an example of a plurality of sensors of one embodiment.

A Plurality of Sensors:

FIG. 8 shows for illustrative purposes only an example of a plurality of sensors of one embodiment. FIG. 8 shows the sexual wellness kits app includes a plurality of sensors 800. The plurality of sensors detects and measures a partner's vital signs and other physiological factors related to their wellness levels. The plurality of sensors includes pulse sensors to measure heart rate 810, respiration sensor to measure breathing rate 820, blood pressure sensors to measure diastolic and systolic 830 blood pressure levels, and an accelerometer to detect when the user is moving to determine if vital signs are within predetermined limits for certain activities 840. The sexual wellness kits app 160 of FIG. 1 includes a digital processor to compare vital signs with user indicated symptoms 850. The symptoms of some conditions impact vital signs for example rising or lowing blood pressure. The sexual wellness kits app 160 of FIG. 1 processor searches a stored listing of symptomatic related effects on vital signs. The processor matches any stored vital signs symptomatic impacts with those of the partner's detected vital signs to determine if a correlation exists within the noted ranges of the vital signs. If the current vital signs sensor detected measurements are outside the ranges for the symptoms the partner is advised to seek a review by their physician of one embodiment.

Figure 9:
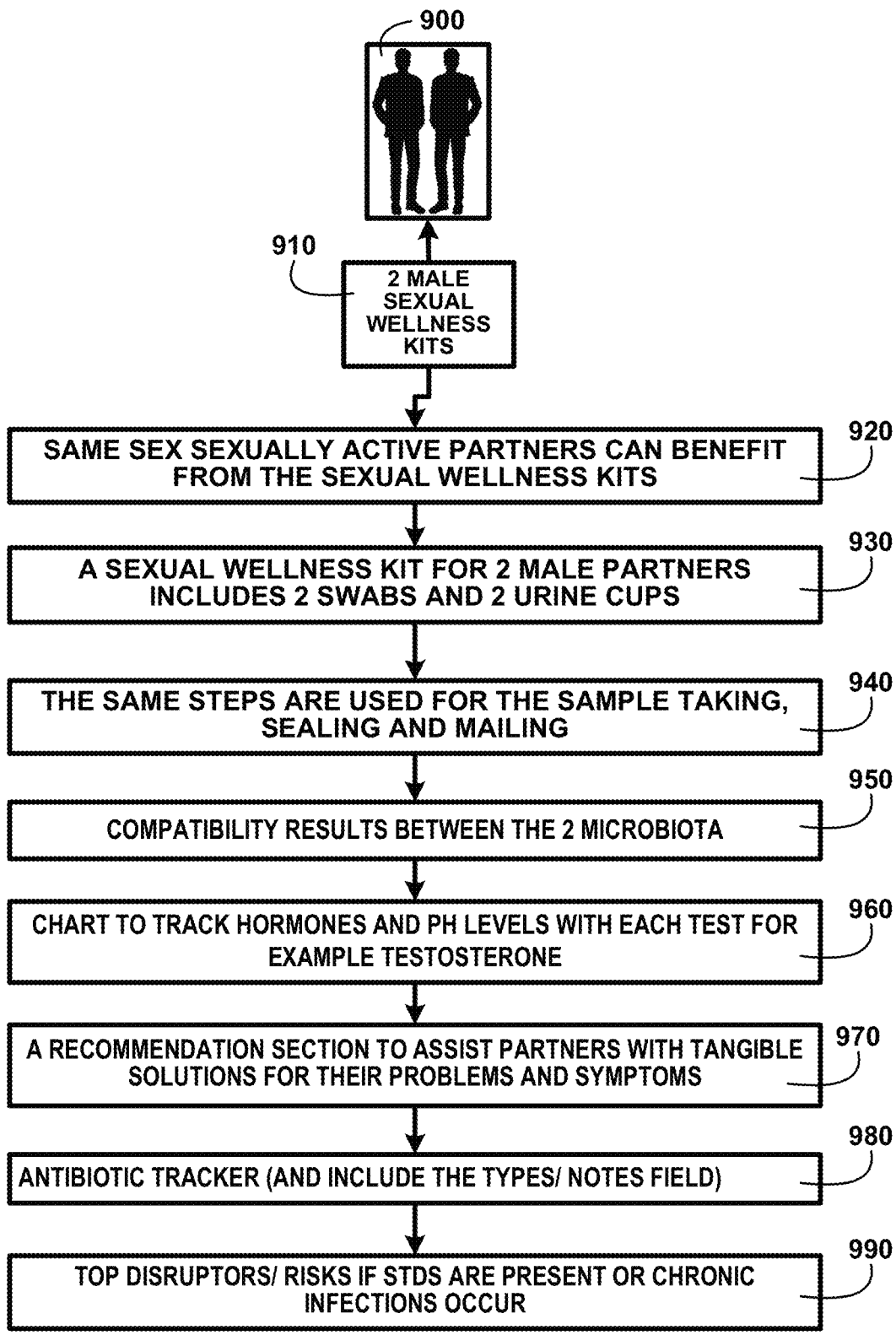
FIG. 9 shows for illustrative purposes only an example of same sex sexually active partners of one embodiment.

Same Sex Sexually Active Partners:

FIG. 9 shows for illustrative purposes only an example of same sex sexually active partners of one embodiment. FIG. 9 shows a couple with two male partners 900 purchasing two male sexual wellness kits 910. Same sex sexually active partners can benefit from the sexual wellness kits 920 to get current testing conveniently and receive results on what may be of concern that have been unanswered and not discussed between the partners. A sexual wellness kit for two male partners includes two swabs and two urine cups 930. The same steps as shown in FIGS. 2 and 3 are used for the sample taking, sealing and mailing 940. The laboratory 120 of FIG. 1 genetic testing will provide compatibility results between the two micro biotas 950. The sexual wellness kits app 160 of FIG. 1 will generate, with at least one of the plurality of processors 141 of FIG. 1, a chart to track hormones and PH levels with each test for example testosterone 960. A recommendation section to assist partners with tangible solutions for their problems and symptoms 970 will be transmitted to the sexual wellness kits app 160 of FIG. 1 on the partner's individual smart phone. The sexual wellness kits app 160 of FIG. 1 will generate separate antibiotic tracker (and include the types/notes field) 980 histories for each partner to keep them informed of their antibiotic use. A listing of top disruptors/risks if STDs are present or chronic infections occur 990 will be transmitted to the sexual wellness kits app 160 of FIG. 1 on the partners individual smart phone of one embodiment.

Figure 10:
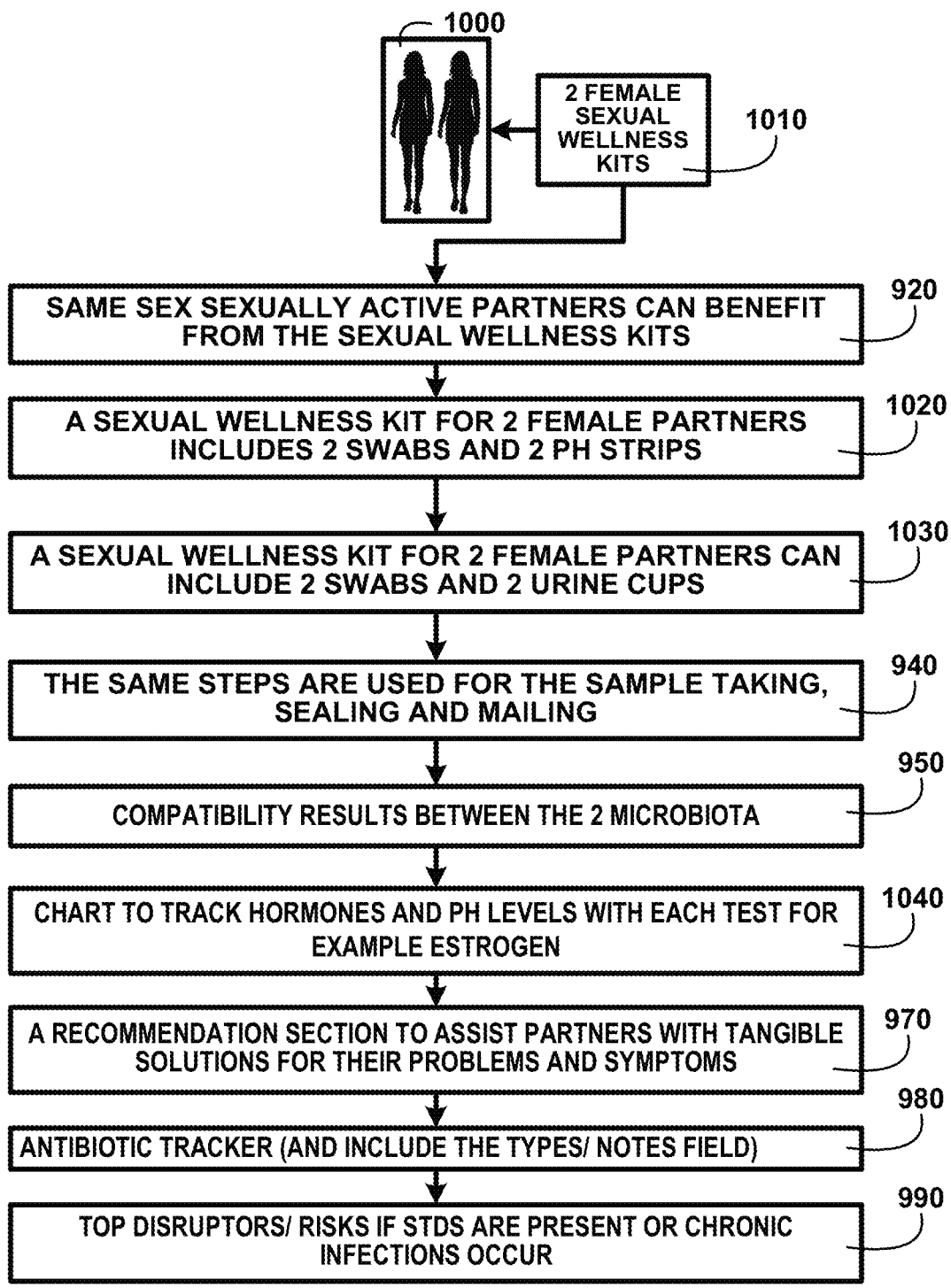
FIG. 10 shows for illustrative purposes only an example of female sexual wellness kits of one embodiment.

Female Sexual Wellness Kits:

FIG. 10 shows for illustrative purposes only an example of female sexual wellness kits of one embodiment. FIG. 10 shows a couple with two female partners 1000 purchasing two female sexual wellness kits 1010. Same sex sexually active partners can benefit from the sexual wellness kits 920. A sexual wellness kit for two female partners includes two swabs and two pH strips 1020. In another embodiment a sexual wellness kit for two female partners can include two swabs and two urine cups 1030. The same steps as shown in FIGS. 2 and 3 are used for the sample taking, sealing and mailing 940.

Compatibility results between the two microbiota 950 will be transmitted to each of the two partners via the sexual wellness kits app 160 of FIG. 1 on their individual smart phones. The sexual wellness kits app 160 of FIG. 1 will generate a chart to track hormones and PH levels with each test for example estrogen 1040. A recommendation section to assist partners with tangible solutions for their problems and symptoms 970 is transmitted to the smart phone of each partner via the sexual wellness kits app 160 of FIG. 1. An antibiotic tracker (and include the types/notes field) 980 on the sexual wellness kits app 160 of FIG. 1 will generate a chart to show each partner their antibiotic use. A listing of top disruptors/risks if STDs are present or chronic infections occur 990 will be transmitted to the sexual wellness kits app 160 of FIG. 1 on the partners individual smart phone of one embodiment.

The foregoing has described the principles, embodiments and modes of operation of the present invention. However, the invention should not be construed as being limited to the particular embodiments discussed. The above-described embodiments should be regarded as illustrative rather than restrictive, and it should be appreciated that variations may be made in those embodiments by workers skilled in the art without departing from the scope of the present invention as defined by the following claims.

What is claimed is:

1. A non-transitory computer-readable medium for determining reproductive compatibility between two partners, comprising instructions stored thereon, that when executed on a processor, perform the steps of:

receiving, by a remote server, an electronic communication having a first partner profile, a second partner profile, a first data set of a first reproductive microbiome test sample extracted from human cells from a first swab containing vaginal mucosa from the vagina of the first partner, and a second data set of a second reproductive microbiome test sample extracted from human cells from a second swab containing coronal sulcus from male genitalia of the second partner, wherein the first and second partner profiles contain demographic information and medical condition symptoms of the first and second partners, respectively;

comparing, with a processor coupled to the remote server, the first and second data sets to generate first and second reproductive microbial compositions comprising similarities, differences, normalities, and abnormalities between the first and second profiles;

converting, with the processor, the first and second reproductive microbial compositions into first and second characterization profiles based on the similarities, differences, normalities, and abnormalities between the first and second profiles;

identifying, with DNA genetic sequencer processor, DNA genetic identification of microbiome genetic material of microbiota microorganisms in the first and second characterization profiles related to reproductive genetic disorders dispositions;

comparing, with the processor, the first and second characterization profiles with each other and to known baseline genetic data to identify shared microbes between the first and second samples, existing pathogens in the first and second reproductive microbiome samples, to distinguish between potentially different microbial species contributing to any imbalances in the first and second reproductive microbiome samples, and using the identified reproductive genetic disorder dispositions to determine reproductive compatibility between the two partners and potential inherited reproductive genetic disorder dispositions;

generating, with the processor, an analysis comprising the identified shared microbes, existing pathogens, differences associated with the known baseline genetic data, the imbalances in the first and second reproductive microbiome samples, and personalized compatibility recommendations with optimized reproductive microbiome information for each of the first and second partners;

comparing, with the DNA genetic sequencer processor, the first and second DNA genetic sequencer results and microbiota microorganisms identified of the first and second characterization profiles with each other and to known baseline genetic data to identify shared microbes between the first and second samples, existing pathogens in the first and second reproductive microbiome samples, to distinguish between potentially different microbial species contributing to any imbalances in the first and second reproductive microbiome samples, and using the identified reproductive genetic disorder dispositions to determine reproductive compatibility between the two partners and potential inherited reproductive genetic disorder dispositions;

generating, with the processor, an analysis comprising the identified shared microbes, existing pathogens, differences associated with the known baseline genetic data, the imbalances in the first and second reproductive microbiome samples, and personalized compatibility recommendations data with optimized reproductive microbiome information for each of the first and second partners; and displaying, on a user graphical interface of a smartphone, analytic results including the personalized compatibility recommendations data for each of the first and second partners, including treatment recommendations for reproductive incompatibilities to increase the reproductive compatibility between the partners.

2. The non-transitory computer-readable medium for determining reproductive compatibility between two partners, comprising instructions stored thereon, that when executed on a processor, perform the steps of claim 1, further comprising identifying, with the processor, a genetic disposition analysis including potential genetic disorders of future conceived children by the partners.

3. The non-transitory computer-readable medium for determining reproductive compatibility between two partners, comprising instructions stored thereon, that when executed on a processor, performs the steps of claim 1, further comprising scanning, with the processor, the electronic communication for each partner's genetic disposition.

4. The non-transitory computer-readable medium for determining reproductive compatibility between two partners, comprising instructions stored thereon, that when executed on a processor, perform the steps of claim 1, further comprising generating, with the processor, a comparison to further identify microbial interactions between the reproductive microbiomes of the first partner and the second partner with the processor.

5. The non-transitory computer-readable medium for determining reproductive compatibility between two partners, comprising instructions stored thereon, that when executed on a processor, perform the steps of claim 1, further comprising storing first information and second information and a data of genetic disorders on the non-transitory computer-readable medium.

6. The non-transitory computer-readable medium for determining reproductive compatibility between two partners, comprising instructions stored thereon, that when executed on a processor, perform the steps of claim 1, further comprising generating, with the processor, a list of treatable symptoms by extracting from the electronic communication stored on the non-transitory computer-readable medium the symptoms of the first and second partners.

7. A system for determining reproductive compatibility between two partners, comprising:
a) a remote server configured to receive an electronic communication having a first partner profile, a second partner profile, a first data set of a first reproductive microbiome test sample extracted from human cells a first swab containing vaginal mucosa from the vagina of the first partner, and a second data set of a second reproductive microbiome test sample extracted from human cells a second swab containing coronal sulcus from male genitalia of the second partner, wherein the first and second partner profiles contain demographic information and medical condition symptoms of the first and second partners, respectively;
b) a processor coupled to the remote server configured to: compare the first and second data sets to generate first and second reproductive microbial compositions comprising similarities, differences, normalities, and abnormalities between the first and second profiles, converting, with the processor, the first and second reproductive microbial compositions into first and second characterization profiles based on the similarities, differences, normalities, and abnormalities between the first and second profiles;
identify, with a DNA sequencer processor, DNA genetic identification of microbiome genetic material of microbiota microorganisms in the first and second characterization profiles related to reproductive genetic disorder dispositions that may be responsible for a partner's medical conditions or diseases;
compare the first and second characterization profiles with each other and to known baseline genetic data to identify shared microbes between the first and second samples, existing pathogens in the first and second reproductive microbiome samples, to distinguish between potentially different microbial species contributing to any imbalances in the first and second reproductive microbiome samples, and using the identified reproductive genetic disorder dispositions to determine reproductive compatibility between the two partners and potential inherited reproductive genetic disorder dispositions; and
generate an analysis comprising compatibility recommendation data to assist partners with tangible solutions for their problems and symptoms including the identified shared microbes, existing pathogens, differences associated with the known baseline genetic data, and imbalances in the first and second reproductive microbiome samples; and
c) at least one mobile device wirelessly coupled to the remote server having a graphical user interface and a mobile application configured to receive from the remote server the compatibility recommendation data and personalized recommendations for configuration in the mobile application and display on the graphical user interface, including treatment recommendations for reproductive incompatibilities to increase the reproductive compatibility between the partners.

8. The system for determining reproductive compatibility between two partners of claim 7, wherein the DNA genetic sequencer processor is further configured to identify a genetic disposition including potential genetic disorders of future conceived children by the partners.

9. The system for determining reproductive compatibility between two partners of claim 7, wherein the processor is further configured to scan the electronic communication for each partner's genetic disposition.

10. The system for determining reproductive compatibility between two partners of claim 7, wherein the processor is further configured to generate a comparison to further identify microbial interactions between the reproductive microbiomes of the first partner and the second partner with the processor.

11. The system for determining reproductive compatibility between two partners of claim 7, wherein the processor is further configured to store first information and second information and a library of genetic disorders on the non-transitory computer-readable medium.

12. The system for determining reproductive compatibility between two partners of claim 7, wherein the processor is further configured to generate a list of treatable symptoms by extracting from the electronic communication stored on the non-transitory computer-readable medium the symptoms of the first and second partners.

13. The system for determining reproductive compatibility between two partners of claim 7, wherein the processor is further configured to create a communication with a recommendation section to assist partners with solutions for their medical conditions and symptoms.

\* \* \* \* \*